United States Patent
Rozenfeld et al.

(10) Patent No.: US 10,285,571 B2
(45) Date of Patent: May 14, 2019

(54) PRE-SHAPED RIGID PORT

(71) Applicant: LARYNGOPORT LTD., Jerusalem (IL)

(72) Inventors: Revital Rozenfeld, Nes Ziyona (IL); Nir Barkai, Kfar Saba (IL); Yonatan Lahav, Timorim (IL); Moshe Hain, Jerusalem (IL); Mark Sahar, Holon (IL)

(73) Assignee: LARYNGOPORT LTD., Jerusalem (IL)

( * ) Notice: Subject to any disclaimer, the term of this patent is extended or adjusted under 35 U.S.C. 154(b) by 642 days.

(21) Appl. No.: 14/437,564

(22) PCT Filed: Oct. 24, 2013

(86) PCT No.: PCT/IL2013/050864
§ 371 (c)(1),
(2) Date: Jul. 16, 2015

(87) PCT Pub. No.: WO2014/064698
PCT Pub. Date: May 1, 2014

(65) Prior Publication Data
US 2015/0327757 A1 Nov. 19, 2015

Related U.S. Application Data

(60) Provisional application No. 61/718,205, filed on Oct. 25, 2012.

(51) Int. Cl.
*A61B 1/267* (2006.01)
*A61B 1/00* (2006.01)
(Continued)

(52) U.S. Cl.
CPC ............ *A61B 1/00154* (2013.01); *A61B 1/06* (2013.01); *A61B 1/267* (2013.01); *A61B 90/90* (2016.02);
(Continued)

(58) Field of Classification Search
CPC ......... A61B 1/24; A61B 1/267; A61B 1/2676; A61B 1/273; A61B 1/2733; A61B 1/2736;
(Continued)

(56) References Cited

U.S. PATENT DOCUMENTS 4,553,540 A * 11/1985 Straith .............. A61M 16/0488
128/200.26
6,095,972 A 8/2000 Sakamoto
(Continued)

FOREIGN PATENT DOCUMENTS

CN 102647936 A 8/2012
EP 1062963 12/2000
(Continued)

*Primary Examiner* — Anu Ramana
(74) *Attorney, Agent, or Firm* — The Roy Gross Law Firm, LLC; Roy Gross

(57) ABSTRACT

The present invention provide a pre-shaped port, at least partially introduced into a body cavity, comprising a body characterized by a distal end and a proximal end; said body comprising at least one throughgoing channel enabling introduction of at least one surgical tool; said distal end comprises at least one extension; wherein said extension is adapted to provide mechanical support to a distally located organ within said body cavity.

20 Claims, 10 Drawing Sheets

(51) Int. Cl.
*A61B 1/06* (2006.01)
*A61M 16/04* (2006.01)
*A61B 90/96* (2016.01)
*A61B 90/90* (2016.01)
*A61B 90/98* (2016.01)

(52) U.S. Cl.
CPC .............. *A61B 90/96* (2016.02); *A61B 90/98* (2016.02); *A61M 16/0493* (2014.02); *A61M 16/0495* (2014.02); *A61M 2205/60* (2013.01); *A61M 2209/088* (2013.01)

(58) Field of Classification Search
CPC ............ A61M 16/049; A61M 16/0493; A61M 16/0495; A61M 16/0497
See application file for complete search history.

(56) References Cited

U.S. PATENT DOCUMENTS

| | | | |
|---|---|---|---|
| 6,439,232 B1 * | 8/2002 | Brain | A61M 16/04 128/200.26 |
| 6,843,769 B1 | 1/2005 | Gandarias | |
| 8,202,215 B2 | 6/2012 | Xiao et al. | |
| 2007/0106121 A1 | 5/2007 | Yokota et al. | |
| 2011/0130627 A1 | 6/2011 | McGrail | |
| 2011/0196203 A1 | 8/2011 | Xiao | |
| 2012/0004504 A1 | 1/2012 | Frassica et al. | |

FOREIGN PATENT DOCUMENTS

| | | |
|---|---|---|
| GB | 2431539 | 4/2007 |
| JP | S6212301 U | 1/1987 |
| JP | H0622909 A | 2/1994 |
| JP | H07163516 A | 6/1995 |
| JP | H08510938 A | 11/1996 |
| JP | H09299328 A | 11/1997 |
| JP | 2007117114 A | 5/2007 |
| JP | 2007151885 A | 6/2007 |
| JP | 2008228783 A | 10/2008 |
| JP | 2008289520 A | 12/2008 |
| JP | 2009066266 A | 4/2009 |
| JP | 2011224376 A | 11/2011 |

\* cited by examiner (AREA A)

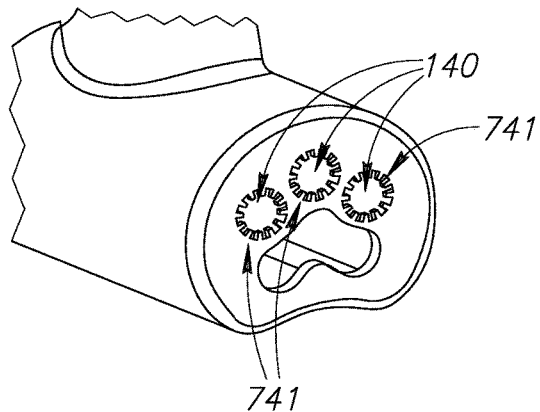
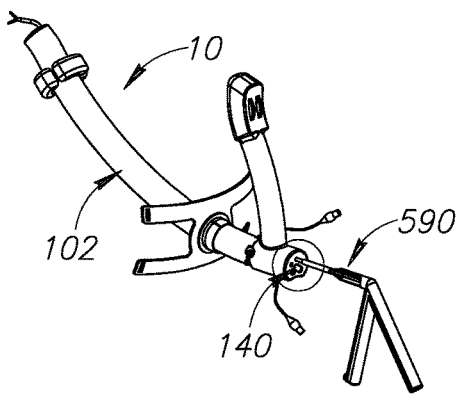
FIG.8A   FIG.8B
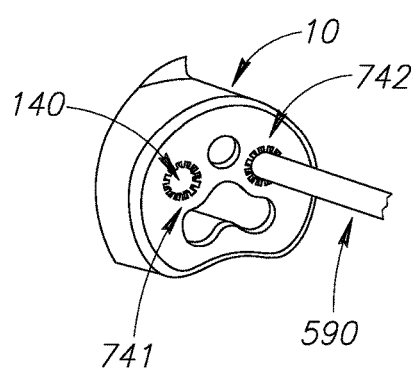
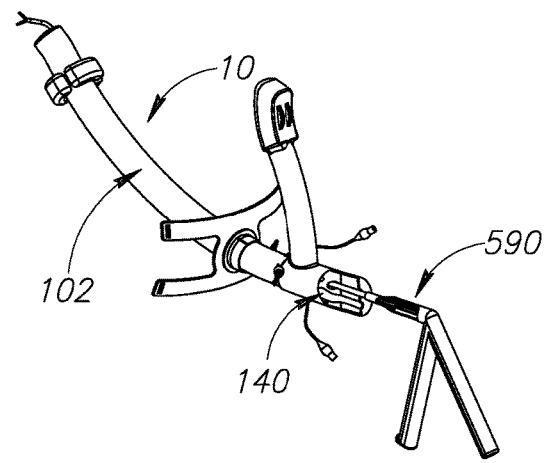
FIG.8C   FIG.8D
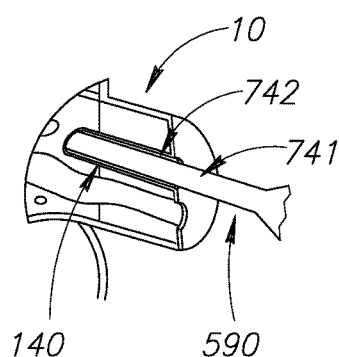
FIG.8E (AREA A)

(AREA A)

(AREA A)

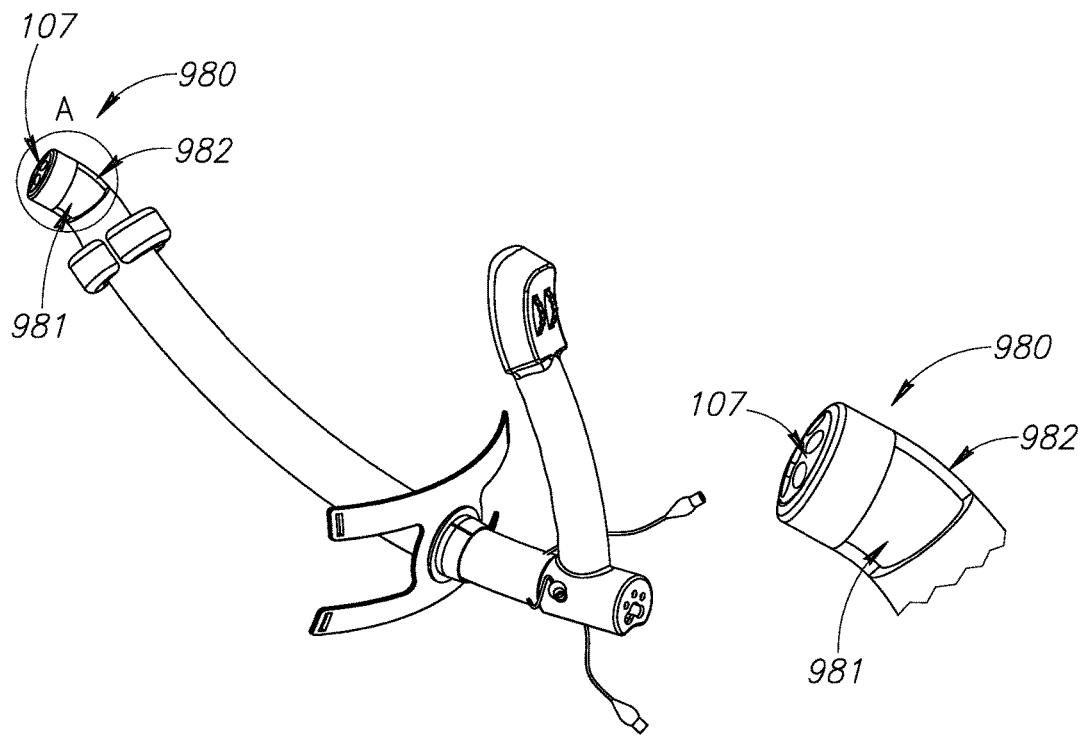
FIG.10C
FIG.10D
(AREA A)
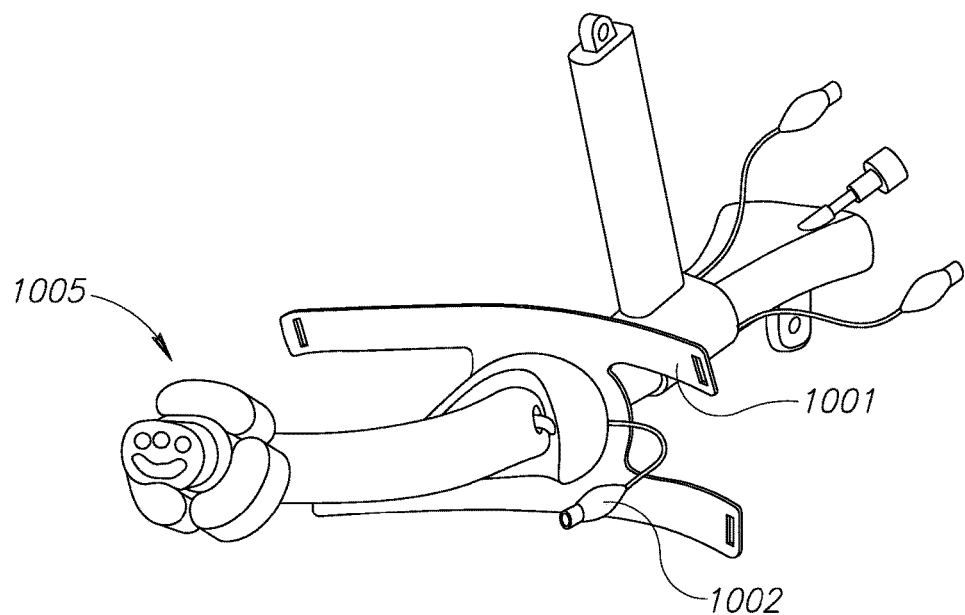
FIG.11A

PRE-SHAPED RIGID PORT

FIELD OF THE INVENTION

This invention relates to devices adapted for use in laryngeal microsurgery. In particular and preferably, it relates to a rigid, semi-rigid, semi-flexible, modular platform for use in such surgery.

BACKGROUND OF THE INVENTION

The surgical method most commonly used today for procedures on the larynx and hypopharynx is Direct Micro-Laryngoscopy (DML). This method enables both direct view of the region upon which the procedure is being performed via a rigid laryngoscope, the use of a binocular microscope and the use of a variety of surgical instruments.

A number of inventions disclosing means for positioning surgical devices for use in laryngeal surgery are known. U.S. Pat. No. 5,894,840 and European Pat. No. EP1062963 are examples of disclosures of means for fixing an endotracheal tube. These devices ensure that the endotracheal tube will remain in place and the patient's airway will remain open during surgery. A laryngoscope that will allow passage of microsurgical tools and maintain the patient's airway open but that allows the patient to remain in a natural body position and that helps prevent the risk of tissue damage common in typical laryngoscopic procedures, thus remains a long-felt, yet unmet, need.

SUMMARY OF THE INVENTION

It is an object of the invention to disclose to a rigid, semi-rigid, semi-flexible, modular platform for use in surgery, particularly laryngeal microsurgery.

It is another object of the invention to disclose a pre-shaped port, comprising a body characterized by a distal end and a proximal end; said body comprising at least one throughgoing channel enabling introduction of at least one surgical tool; wherein said distal end comprises an extension adapted to provide mechanical support to a distally located organ.

It is another object of the invention to disclose a method for surgery, comprising: (a) obtaining a pre-shaped port, comprising a body characterized by a distal end and a proximal end; said body comprising at least one throughgoing channel enabling introduction of at least one surgical tool; (b) obtaining at least one surgical tool; (c) inserting said port into a body passage of a patient; and (d) inserting said surgical tool into said port; wherein said distal end of said pre-shaped port comprises an extension adapted to provide mechanical support to a distally located organ.

BRIEF DESCRIPTION OF THE DRAWINGS

The invention is now described with reference to the drawings, wherein

FIGS. 7-9 illustrate embodiments (not to scale) of hand-shaking interfaces;

FIGS. 11A-D illustrates the engagement interface of the fixation and stabilization element.

DETAILED DESCRIPTION OF THE PREFERRED EMBODIMENTS

Figure 1A:
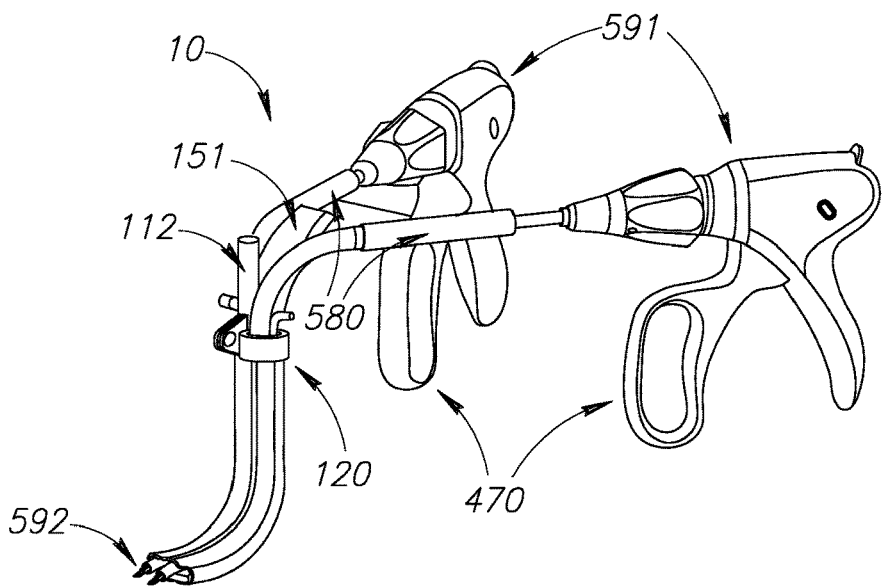
FIG. 1A-B illustrates (not to scale) the construction of a laryngoscope or port according to an embodiment of the invention.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

The present invention provides a pre-shaped port, preferably S-shaped, comprising a body characterized by a distal end and a proximal end; said body comprising at least one throughgoing channel enabling introduction of at least one surgical tool; wherein said distal end comprises an extension adapted to provide mechanical support to a distally located organ.

According to one embodiment, the port is a laryngoscope. According to another embodiment, the organ supported is the epiglottis.

According to the core concept of the present invention the port is rigid port, a semi-rigid port, a semi-flexible port and any combination thereof.

The port of the present invention preferably comprises a multi channel rigid trans-oral port with, in some embodiments, a circular cross-section, a pre-shaped multi-channel device to be placed trans-orally, partially in the hypopharynx and partially in the oral cavity in a bent fashion.

The core concept behind the present invention is to provide a rigid, pre-shaped port with a support rim at its distal end and at least on throughgoing channel adapted to allow passage therethrough of at least one tool. Tools are preferably flexible, but can be semiflexible.

In preferred embodiments, a single handle controls both the port and at least one function of the distal end of the tool. In other embodiments, the there are separate controls for the port and for the at least one function of the distal end of the tool.

In some embodiments of the present invention, the port also comprises an interface that enables the actuation of only allowable tools. Thus, tools that are not "allowed" would not be able to be actuated. Actuation mechanisms can be either passive or active. It is to be emphasized that having an interface to allow tools is an option; in preferred embodiments, all tools with outside diameter no larger than the diameter of a channel are allowed tools.

In some embodiments of the present invention, the articulated tools are activated by means of an interface between the port and the tool, such that only tools which are identified (by means of said interface) would be able to be introduced into the port and be actuated.

It should be emphasized that the following description discloses a port and the area of the larynx; however, similar ports that can be used in different anatomic area (e.g., trans-rectum colon surgery, laparoscopic surgery, intestinal surgery or examination where the point of entry is the anus, uterine surgery or examination where the point of entry is the vagina, bladder surgery or examination via the urethra and prostate surgery or examination via the urethra, and NOTES (Natural Orifice Transluminal Surgery)) are enclosed within the scope of the present invention.

The term laryngoscope refers hereinafter to any port adapted to introduce surgical tools into any body cavity.

The port of the present invention enables the following:

(1) provide exposure of the surgical or treatment area by causing widening of the space directly above the larynx (hypopharynx) to create a "working area", analogous to the inflated abdominal cavity in laparoscopy;

(2) provide access by allowing passage both alongside the port, for example, of an endotracheal tube, and through the port of optics and of a number of surgical tools; and, (3) provide precision, tremor free surgery or treatment by lending support, stability and anchorage to the equipment both within the throughgoing channels and at the port's distal end, thereby allowing stable, precise laryngeal surgery or treatment by ensuring smooth movement of the surgical tools through the channels in the port.

If the port is used as a laryngoscope, the same is disposable and is preferably about 25 cm to about 30 cm in length and about 18 mm to about 35 mm in diameter, although the diameter may vary at different parts of the laryngoscope to be better accommodated to the anatomy of the mouth and throat.

Furthermore, the port, as provided by the present invention, is biocompatible and safe for working in a laser treatment environment.

In use, the proximal end of the port (e.g., laryngoscope) extends through the patient's mouth and outside the teeth and lips to allow easy access for the operator or operators. The distal end is situated either just superior or just inferior to the tip of epiglottis, approximately 2 cm above the vocal cords.

The present invention relates to laryngeal medical procedures, such as treatment or surgery. The general method of carrying out laryngeal medical procedures using the port as provided by the present invention is as follows:

a. Intubate the patient with a small diameter endotracheal tube (#5.5-6.5) and induce anesthesia.

b. Insert the port (i.e., the laryngoscope) atraumatically by gliding it along the endotracheal tube until its distal end has passed beyond the base of tongue. An anesthesiologist's laryngoscope (used for intubation) may be employed to aid insertion.

c. Pass an endoscope through its designated channel in the port and view the surgical field so obtained. The surgeon sees the picture on a monitor.

d. Fine tune the position of the port using a displayed view of the surgical field.

e. Once the desired field is obtained, inflate the distal inflation mechanism to expand the field and stabilize the port.

f. Fasten and fixate the port to the head using the mouthbite (refers hereinafter as a fixation element) and to the designated head fixation mechanism such that both the head of the patient and the laryngoscope are immobile. The head fixation mechanism can be a head rest, a head support pillow, an external stand, and any combination thereof.

g. Optionally, secure to the operating bed a designated stand, which holds the proximal ends of the tools, endoscope, laser and suction.

h. Using the current best practice position—behind and above the patient's head—perform the medical procedure using the specially designed articulating tools, or laser.

i. Advance a first set of tools through the channels in the port.

ii. Perform the medical procedure, changing tools as needed.

a. When the laser is used, it will pass through one channel and a small suction channel will be connected to continuous suction so as to clear smoke and vapors.

b. One of the channels can be used to insert neuropads for hemostasis and also as the port for removal of resected tissue. Optionally, specimens can be put in special bag before removal to avoid spillage and seeding—similar to what is commonly done in laparoscopy.

c. For embodiments of the port with distal articulation (disclosed hereinbelow), the surgeon may, during the medical procedure, adjust the view by using the articulation abilities of the distal tip of the port (Up to about 30 degrees to each side). For embodiments without distal articulation, the field of view can be adjusted using the camera's articulation capability.

3. Complete the procedure by:

a. Deflate the inflation mechanism and remove the stabilization straps for the head and port.

b. Remove the port from the oral cavity.

The term "about" refers hereinafter to a range of 25% below or above the referred value.

The term "surgical tool" refers hereinafter to any tool that can be at least partially inserted through a port. Surgical tools can be broadly divided into two classes, surgical instruments, which are used during surgical procedures, and treatment tools, which are used during treatment of medical conditions. Typical examples of surgical instruments comprise scalpels, forceps, hemostats and clamps. Typical examples of treatment tools comprise syringes, hypodermic needles, applicators and lasers, although lasers can also function as surgical instruments.

Typical examples of surgical procedures include removal of tumors and repair of torn vocal cords. Typical examples of treatment of medical conditions include injection treatments for the vocal cords.

The term "epiglottis" refers hereinafter to a flap that is made of elastic cartilage tissue covered with a mucous membrane, attached to the entrance of the larynx.

The term "allowed tool" refers hereinafter to any tool which can engage with the port and thus can be actuated when introduced through the same. In some embodiments of the present invention, a tool is an allowed tool if its outer diameter is no larger than the diameter of the port. In other embodiments, the port comprises an identification interface, which identifies whether a surgical tool is an allowed tool. The identification interface can be either passive or active. Once a tool has been identified as "allowed", the same can engage with the port and can be actuated. It should be emphasized that once the tool has been identified as "allowed", the same can either be introduced into the port and/or can be actuated.

The term "passive interface" refers hereinafter to any passive means that ensures a proper engagement between the tool and the port (and the identification of the tool as allowed) before the tool can be activated and used. For a passive interface, there is no need for any part (either in the port or the tool) to be active in order to provide the identification and engagement.

The term "active interface" refers hereinafter to any active means that ensures a proper engagement between the tool and the port (and the identification of the tool as allowed) before the tool can be activated and used. For an active interface, a movement of a part within either the port or the tool is required in order to provide the identification and engagement.

The term "laryngoscope" refers hereinafter to any laryngoscope (used in laryngeal treatment or surgery) or any port to be used mainly for introduction of surgical tools, including surgical instruments or treatment tools, into a body cavity for performing and facilitating a medical procedure, which can be surgery or a treatment procedure.

Reference is now made to FIG. 1, which illustrates (not to scale) a port of the present invention. FIG. 1A illustrates one embodiment 10 of the invention. In this embodiment, the port (10) is generally S-shaped. It can be made of any suitable biocompatible material. The upper part of the S comprises, at the proximal end of the port, two connectors adapted to be connected to handles (591) to control motion of the tools (592). The control portion (470) of the handles (591), in the embodiment shown, comprises a closing mechanism, adapted to close the tools (592). The port (10) further comprises at least one throughgoing channel; one such channel (151) is adapted to accept a lighting means, as described hereinbelow.

In preferred embodiments, the tools are flexible tools, although they can be semi-flexible.

Preferred embodiments, such as that shown in FIG. 1A, comprise an exterior groove adapted to hold an intubation tube (112) which enables passage of air past the port so that the patient can breathe.

Figure 1B:
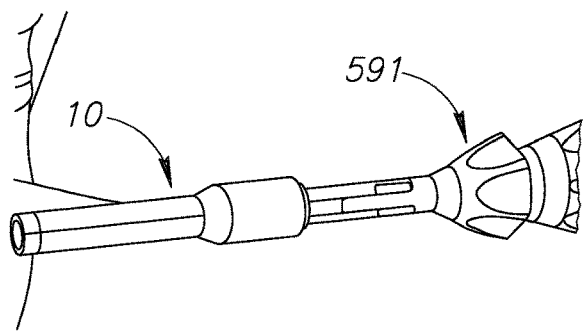

FIG. 1B illustrates, in an out-of-scale manner the connection between the handle (591) and the port (10). In this embodiment, another button has been added, which fits into the application port of the tool. The interface enables insertion of a tool into and out of the port and further enables rotation of the tool, when the same is fitted into the interface.

The diameter of the body is chosen to be appropriate for the size of the patient's oral cavity and throat, while the length is chosen to be appropriate for the patient and the type of medical procedure being performed. In preferred embodiments of the invention, the port is provided in a variety of standard sizes.

In some embodiments, the port comprises a body with cross-sectional shape selected from a group consisting of triangular, trapezoidal, rectangular, rhomboidal, polygonal, oval, elliptical, and any combination thereof.

In some embodiments, the cross-sectional shape of the port is similar throughout the length of the port. In other embodiments, the cross-sectional shape differs in different parts of the port. An illustrative example of an embodiment of a port with different cross-sections in different parts is the embodiment (10) of the port of FIGS. 1A-B, which comprises a generally cylindrical cross-section in the central and distal regions, and generally circular cross-sections in the proximal portion.

Figure 2:
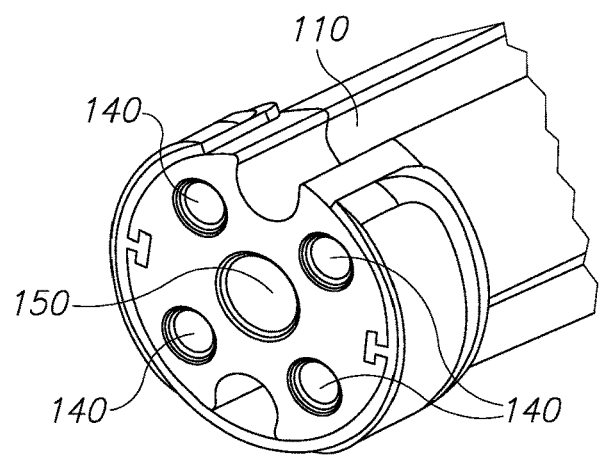
FIGS. 2-6 illustrate views (not to scale) of the distal end of the laryngoscope or port according to embodiments of the invention.

In reference to FIG. 2, the body further comprises a plurality of longitudinal channels through the length of its interior. In preferred embodiments of the larygoscope or port, it comprises a central channel (140) and a plurality of other channels 150. The diameter of the central channel (140) is adapted for accommodation of an endoscopic camera and a light source. The diameters of the other channels (150) are adapted to accommodate other microsurgical tools. FIG. 2 also shows the intubation groove (110).

In some embodiments, the channels further comprise mating interfaces (described hereinbelow) providing a handshake interface to allow the endoscopic camera and microsurgical tools to slide through the channels, and then to reversibly ensure that the camera and tools are properly engaged within the channels, enabling proper positioning of the tools and maintenance of the tools in their desired locations.

Alternatively, the channels further comprise mating mechanisms providing a handshake interface to allow the endoscopic camera and microsurgical tools to slide through the channels, and then to lock the camera and tools in place, enabling proper positioning of the tools and maintenance of the tools in their desired locations.

According to some embodiments of the present invention, the handshake interface between the port and a surgical tool can be performed in at least one channel. Handshaking can be individual, with each tool handshaking within a channel, or it can be multiple, with handshaking activating a plurality of tools in a plurality of channels.

According other embodiments, the central channel can be coupled to an external light source via coupler 140 and, for example, can enable the passage of optical fibers to the distal end of the same.

Figure 3A:
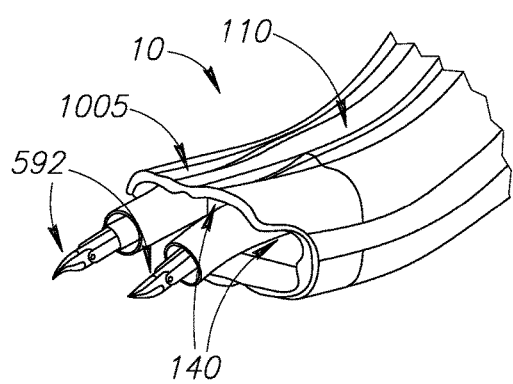
Figure 3B:
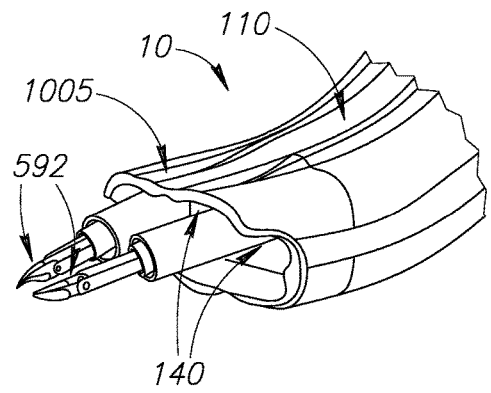

FIG. 3A-B illustrates, in an out-of-scale manner, two views of the distal end of the port (10), showing two tools (592) and the connection ports (140) by which the tools are connected to the port and which enable control of at least one degree of freedom of the tools by the handles (not shown). Said degree of freedom controlled by the port is selected from a group consisting of activation of the tool, rotation of the distal end of the tool, translation of the distal end of the tool and any combination thereof.

The ports also control activation of the tools. In FIG. 3A, the tools are approximately parallel to each other; in FIG. 3B, they have been rotated towards each other so that their tips almost touch, and also rotated about their longitudinal axes so that they face downward rather than sideways, as they did in FIG. 3A.

FIG. 3A-B also illustrates the groove (110) for the intubation tube; and the extension (1005) adapted to provide support for the epiglottis. It is emphasized that the term "mechanical support" refers hereinafter to at least partially removing the tissue or organ (e.g., the epiglottis) from the field of view and supporting it so that it remains out of the field of view. It can also increase the 'working area' available to the physician.

In preferred embodiments, the extension (1005) can be fixed in place or articulates or can be linearly moved relative to the distal end of the port, as described hereinbelow.

One of the major difficulties in laryngeal surgery is to overcome the difficulties caused by the epiglottis (e.g., constant saliva/mucous drooling; the required need to "lift" and move the epiglottis from its position). Thus, according to one embodiment of the present invention, a roof-like extension 1005 is provided.

The extension 1005 is an extension to the port body which guides the port through the larynx. Furthermore, the extension 1005 provides mechanical support and lifting of the epiglottis. Yet more, due to its construction and design, it shifts away any saliva/mucous drooling from the field of view of the physician.

Figure 4A:
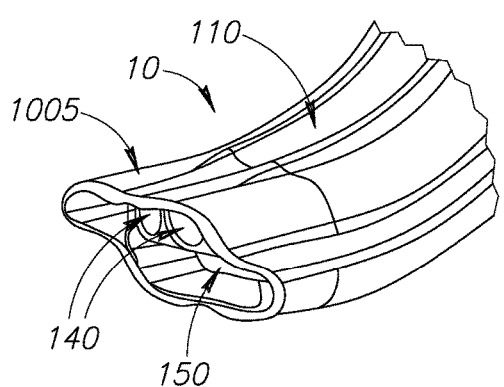
Figure 4B:
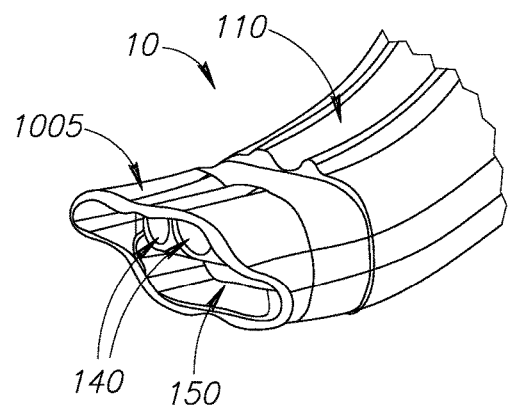

Reference is now made to FIGS. 4A-B, which illustrates an embodiment of the extension (1005) at the distal end of the port (10) in two different positions. In some embodiments, the extension (1005) is rigidly coupled to the rim of the distal end of the port (10), encircling at least a portion of the rim. In said embodiment, the extension (1005) is an integral part of the port.

In preferred embodiments, the extension (1005) articulates with respect to the distal end of the port (10). The articulation can comprise (a) sliding in an out relative to the distal end, so that the distance from the end of the extension (1005) to the distal tip of the port (10) can change; (b) rotation relative to the main longitudinal axis of the port (10), so that the extension (1005) can rotate around the distal tip. In this manner, the longest portion of an extension (1005) can be placed in any desired position with respect to the port (10), for non-limiting example, above it (as illustrated in FIGS. 4A-B), to the side of it, or below it; (c) rotation relative to an axis perpendicular to the main longitudinal axis. In this manner, the extension (1005) can be folded away from the tools (592) or toward them.

In FIGS. 4A-B, the extension (1005) slides with respect to the distal end of the port (10). In FIG. 4A, the extension (1005) is in its fully retracted position, so that the distance from the end of the extension (1005) to the distal tip of the port (10) is a minimum. In FIG. 4B, the extension (1005) has been linearly slid outwards; so that the distance from the end of the extension (1005) to the distal tip of the port (10) is close to its maximum.

FIGS. 4A-B also show the ends of the throughgoing channels (140, 150) and the intubation groove (110).

Figure 5A:
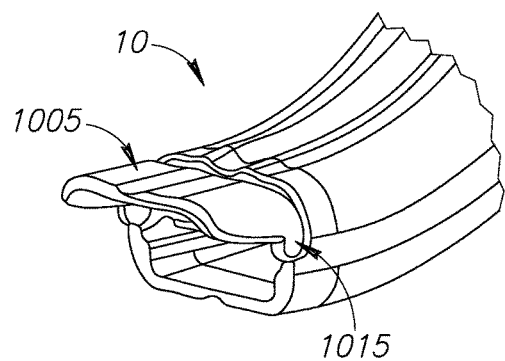
Figure 5B:
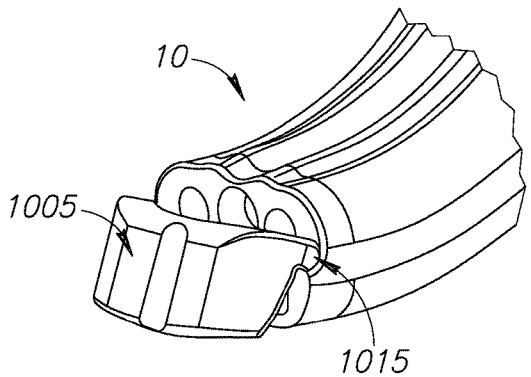

Reference is now made to FIGS. 5A-B, which illustrate an extension (1005) that rotates relative to the distal end of the port (10). In FIG. 4A, the extension (1005) is in its most open position, with the extension (1005) substantially parallel to the top rim of the port (10). In FIG. 4B, the extension (1005) has been bent downwards to approximately its maximum bend, so that the extension (1005) substantially covers the face of the distal end of the port (10). The hinging mechanism in FIGS. 5A-B comprises an integral pivot (1015) on the extension (1005) which fits into a recess on the distal tip of the port (10). In this embodiment, the pivot (1015) is offset from the main body of the extension (1005).

Figure 6A:
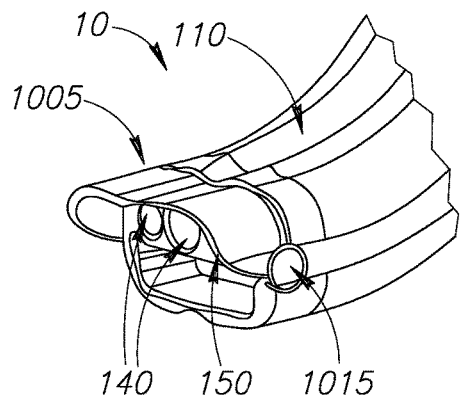
Figure 6B:
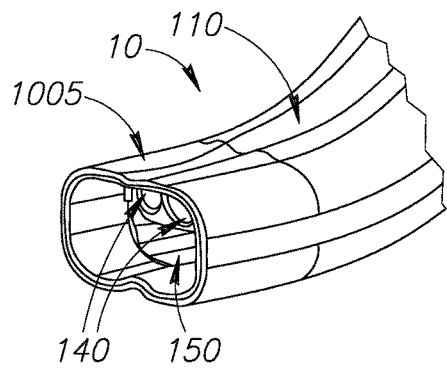

Reference is now made to FIGS. 6A-B, which illustrate two embodiments of the extension (1005) at the distal end of the port (10), The embodiment of FIGS. 6A, like the embodiment of FIGS. 5A-B, has an extension (1005) adapted to rotate about a hinge (1015). However, the hinging mechanism of FIG. 6A comprises a pivot pin (1015) passing through the extension (1005). In this embodiment, the pivot (1015) passes through the main body of the extension (1005).

Other hinging mechanisms (1015) and pivot locations will be obvious to persons skilled in the art. FIG. 6A also shows the intubation groove (110).

The extension (1005) of the embodiment shown in FIG. 6B entirely encircles the rim of the port (10). The ends of the throughgoing channels (140, 150) and the intubation groove (110) are also shown.

It is within the core concept of the present invention wherein said extension is used not only to support an organ (e.g., the epiglottis) but also to "support" the tool going through the channels.

According to said embodiment, by providing said extension, any unwanted movement of the tool out of the boundaries (provided by said extension) will be prevented.

The present invention can additionally comprise an engagement device to ensure that the microsurgical tool must be properly engaged with the port before it can be activated and used. Activation can be mechanical, electrical, electronic, or any combination thereof. It can be (a) passive, requiring no moving parts within either port or tool; (b) active, wherein movement of a part within either port or tool is required for activation; or, (c) operator-assisted, requiring an action by the operator, above and beyond insertion of the tool into the port.

The concept behind the above, is to provide a handshake interface between a port and a surgical tool, such that only when the surgical tool is identified as an "allowed" tool, can the same engage with the port and be actuated. Thus, tools that are not "allowed" could not engage with the port and could not be (a) actuated; or (b) inserted through said port.

According to the above embodiments, the handshake interface between a port and a surgical tool comprises:
(a) at least one surgical tool, adapted to be introduced through a port;
(b) a port having a body, characterized by a distal end and a proximal end interconnected by a main longitudinal axis. The body comprising an identification interface, adapted to identify said surgical tool as an allowed tool; and,
(c) an actuation interface, adapted to actuate said tool once said tool has been identified as an allowed tool; wherein at least a portion of said tool comprises an identification portion such that said tool is defined as allowed and is actuated only after a hand shake match between said identification interface of said port and said identification portion of said tool.

Figure 7A:
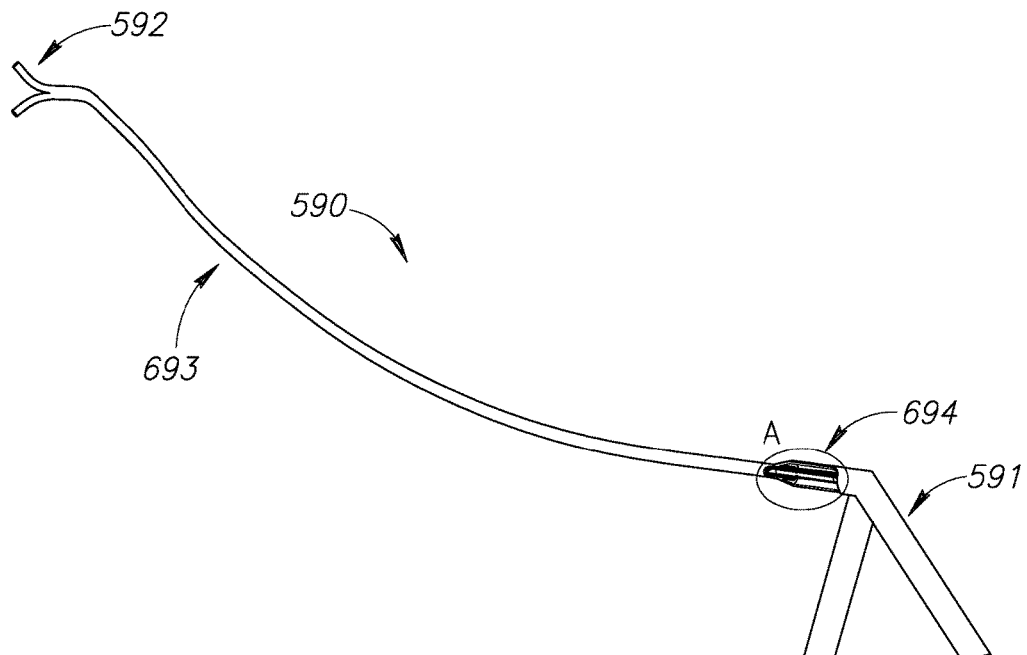
Figure 7B:
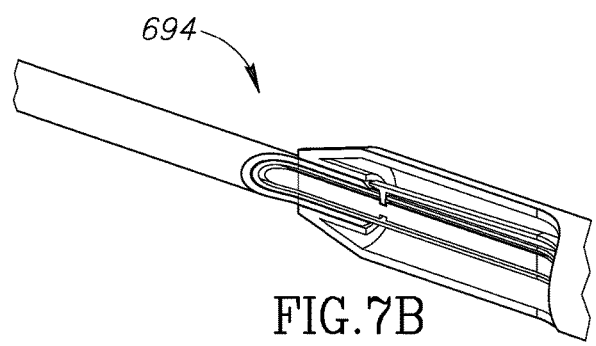

In reference to FIG. 7, an illustration of a tool (690) of the prior art is shown. FIG. 7A shows the entire tool (690), while FIG. 7B shows a close-up of the section of the tool (694), labeled A in FIG. 7A and surrounded by a solid line, where the handle joins the body of the tool. As shown in FIG. 7A, the tool has a handle (591) at the proximal end, a functional distal end (592), and a flexible body (693) of substantially constant cross-section. In FIG. 7A, the section of the tool at the junction of the body and the handle (694) is shown in cutaway view, while the exterior of the remainder of the tool is shown.

In reference to FIG. 7B, a cutaway view of the section of the tool at the junction of the body and the handle (694) is shown, on an enlarged scale. In FIG. 7B, the proximal end of the tool body comprises a substantially constant cross-section along its entire length.

Unlike the prior art tool, FIG. 8 provides an example of a passive activation of the tool.

In reference to FIG. 8, an embodiment of the engagement device provides a non-limiting example of a key-in-lock type passive activation interface, where a section of the microsurgical tool comprises a male profile, fitting a female profile in the port.

As will be described hereinafter, once there is a fit and a match between the port and the tool, the identification interface identifies the tool as allowed and thus, the same can be actuated.

In reference to FIG. 8A, the proximal end of the port is shown, with an embodiment of the channels 140 in which the proximal end of the channels is profiled (741). The microsurgical tool can not be inserted into the channel unless the male profile on the microsurgical tool mates with the female profile 741 on the port.

The microsurgical tool is inserted until its profiled section has passed fully through the profiled section of the port. Once the microsurgical tool has passed fully through the profiled section of the port and its distal end is therefore in the proper position to be used, the microsurgical tool is activated and is free to turn and 360 degrees freely rotate. The tool can not be removed from the port unless the profiles are again matched, prevented unwanted retraction of the tool from the port.

According to some embodiments, activation is possible if there is at least a partial tight fit match between the cross section of at least a portion of a channel in the port and a cross-section of at least a portion of the body of the tool. In this embodiment, activation is possible if part of the perimeter of the cross-section on the tool matches part of the perimeter of the cross-section on the port and, for the remainder of the perimeter, the radius of the tool is less than that of the corresponding radius of the channel. If there is no such match or if the tool perimeter is larger than the corresponding channel perimeter, the distal end of the tool can not reach a proper position to be used and the tool is not activatable.

According to other embodiments, activation is only possible if there is a full tight fit match between the cross section of at least a portion of a channel in the port and a cross-section of at least a portion of the body of the tool. In this embodiment, activation is possible if the shape of the perimeter of the cross-section on the tool matches the shape of the perimeter of the cross-section on the port channel for substantially all of both perimeters. If there is no such match, the distal end of the tool can not reach a proper position to be used and the tool is not activatable.

In reference to FIG. 8B, the port (10) is shown with an inactivated microsurgical tool (590) in position in one of the channels 140. The male profiled section of the microsurgical tool is at least partly within the profiled section of channel 140.

In reference to FIG. 8C, the area within circle A is shown in close-up. In this embodiment, the proximal end of the port and the profiled section of tool 590 are shown. The male profile (742), of the tool, comprises two cogs capable of mating with the female profile (741) in the proximal face of the channel (140) of the port.

In FIG. 8C, the tool is inactivated; the tool cogs of the male profile (742) are engaged with the cogs (741) in the proximal face of the channel (140), thereby preventing rotation of the tool (590).

In reference to FIG. 8D, the port (10) is shown in partial cutaway view with an activated microsurgical tool (590) in one of the channels 140. The proximal portion of the port is shown in cutaway view, so that the interior of the proximal part of the channel can be seen. The male profiled section of the microsurgical tool is wholly within one of the channels 140.

In reference to FIG. 8E, the proximal end of the tool (circle A in FIG. 8D) is shown in close up with an activated microsurgical tool (590) in one of the channels 140. The male profiled section (742) is wholly within the channel 140 and is not in contact with cogs (741) in the proximal face of the channel (140), permitting 360 degrees rotation of the tool within the port (10).

It should be pointed out that the profiled section of the channel (140) can be at the proximal end of the port, at the distal end of the port, all along the channel, in a portion of the body of the port, in the articulated section of the port, just proximal to the articulated section, or any combination thereof.

The profiled section of the tool (590) can be at the proximal end of the tool, at the distal end of the tool, all along the tool, in the body (693) of the tool, or any combination thereof.

It should be pointed out that according to the passive embodiment, illustrated in the above disclosed Figures), the identification interface of the port is the profiled channels, such that only tool having a match fit (or at least partial fit) with said profiled channels of said port, will be defined as "allowed" tool and would be able to be introduced through said port and actuated in the same.

In reference to FIG. 9, a port and tool are shown in an embodiment of an active interface. According to this embodiment, the tool comprises a movable sleeve/collar (841) and a latching mechanism.

The distal end of the handle (591) and a portion of the tool body immediately distal to the handle are shown in cutaway view. In this embodiment, a latching mechanism is lifted in order to activate the tool 590. The latching mechanism (842) comprises an at least partly flexible body portion attached at one end to the tool and a hook portion (843) attached to the free end of the body portion. In some embodiments, the latching mechanism additionally comprises an extension (in this embodiment a distal tip 844) to facilitate moving the hook (843) to the activated state. In the inactivated state, the hook of the latching mechanism physically prevents functioning of the functional distal end of the tool. In the present embodiment, as shown hereinbelow, in the inactivated state, the hook (843) rests in a depression in the tool control transmission mechanism, thereby preventing the tool control transmission mechanism from moving and thus preventing the function distal end of the tool from functioning.

Figures 9A, 9B:
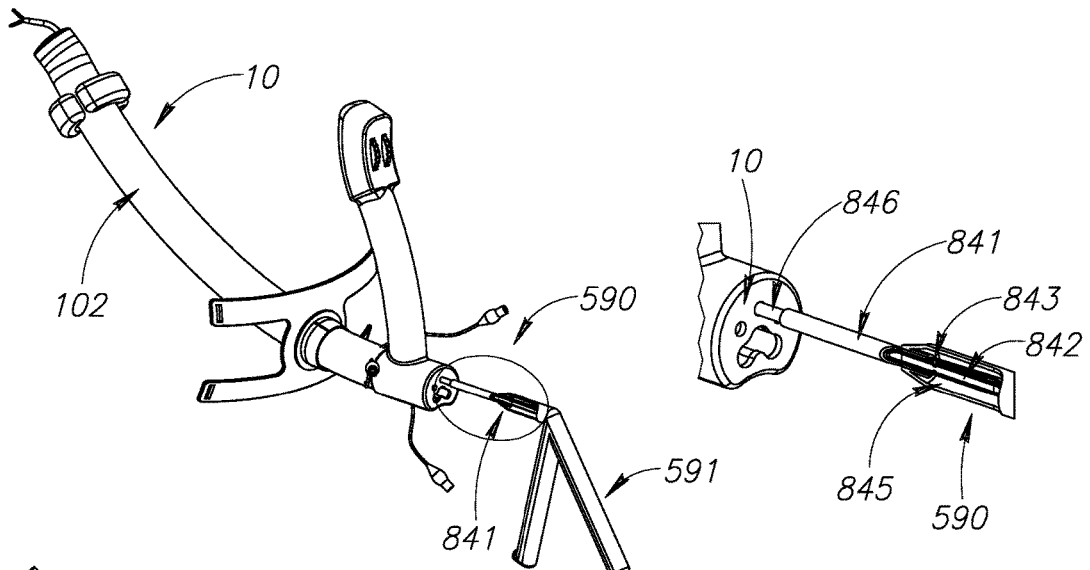

In reference to FIG. 9A, the port (10) is shown with an inactivated microsurgical tool (590) in one of the channels 140. The proximal portion of the port is shown in cutaway view, so that the interior of the proximal part of the channels 140 can be seen.

In reference to FIG. 9B, a close-up of area A (rectangle, FIG. 8A) is shown, illustrating a close-up of the proximal end of the port (10) with an inactivated microsurgical tool (590) in one of the channels 140.

In this embodiment, in the inactivated state, a hook (843) approximately at the distal end of the latching mechanism (842) penetrates the tool wall (846) and rests snugly in a depression (845) in the tool control transmission mechanism, preventing movement of the tool control transmission mechanism relative to the tool wall, thus preventing the functional distal end of the tool from functioning and thereby preventing use of the tool.

Insertion of the tool fully into the port pushes the sleeve against the latching mechanism (842), lifting the hook (843) free of the depression and the hole, thereby activating the tool.

Figure 9C:
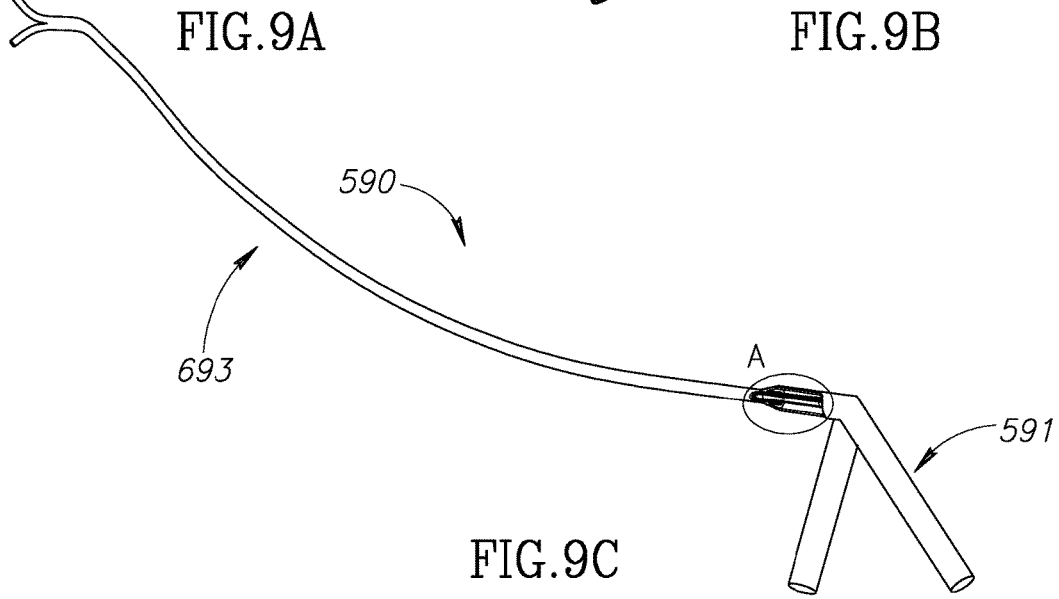

In reference to FIG. 9C, the tool 590 is shown alone. The distal end of the handle (591) and a portion of the tool body (693) immediately distal to the handle are shown in cutaway view.

Figure 9D:
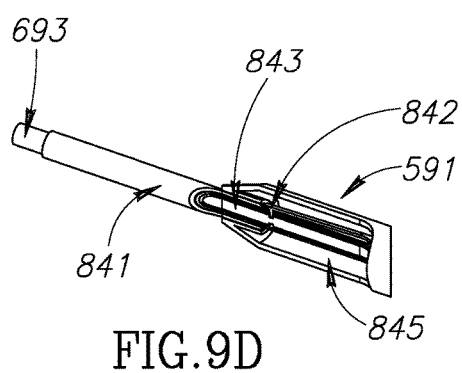

In reference to FIG. 9D, a close-up of area A (rectangle, FIG. 9C) is shown, illustrating a close-up of the distal end of the handle (591) and the proximal end of the tool body (693) with the microsurgical tool (590) in an inactivated state. The hook (843) approximately at the distal end of the latching mechanism (842) penetrates the tool wall (846) and rests snugly in a depression (845) in the tool control transmission mechanism, preventing rotation of the functional distal end of the tool relative to the tool wall and thereby preventing use of the tool.

Figure 9E:
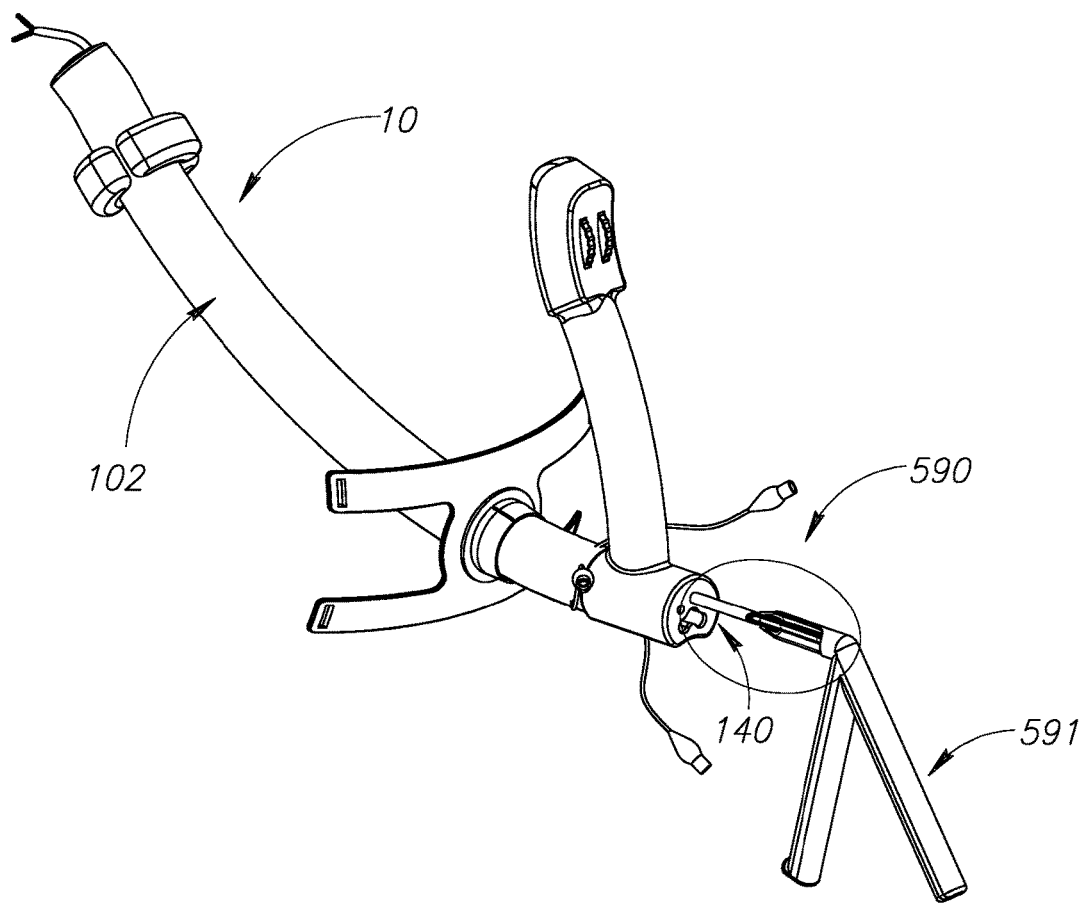

In reference to FIG. 9E, the port (10) is shown with an activated microsurgical tool (590) in one of the channels 140. The proximal portion of the port is shown in cutaway view, so that the interior of the proximal part of the channels 140 can be seen.

Figure 9F:
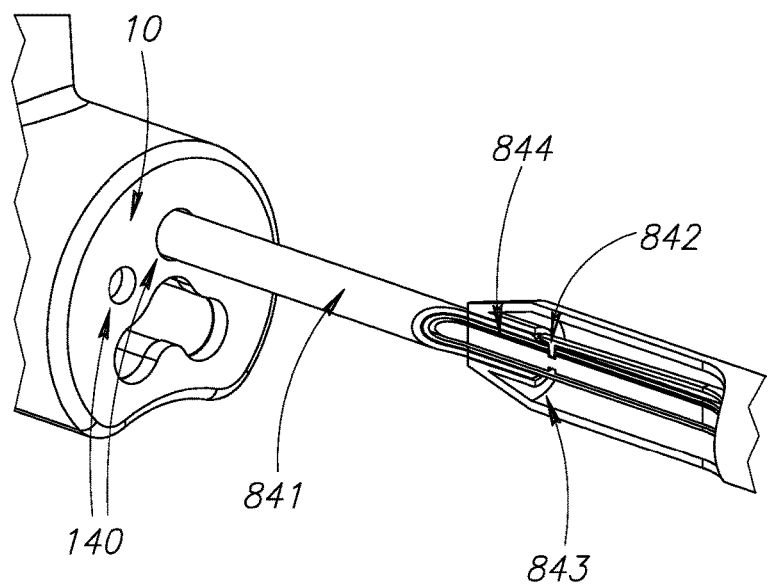

In reference to FIG. 9F, a close-up of area A (rectangle, FIG. 9E) is shown, illustrating a close-up of the distal end of the handle (591) and the proximal end of the tool body (693) with the microsurgical tool (590) in an activated state. The hook (843) approximately at the distal end of the latching mechanism (842) is held clear of the tool wall (846) and the depression (845) in the tool control transmission mechanism by the sleeve (841), thereby permitting rotation of the functional distal end of the tool relative to the tool wall. The extended distal tip (844) of the latching mechanism is adapted to allow smooth ingress of the sleeve (846) into the space between the latching mechanism (842) and the tool wall (846), facilitating raising the hook (843) to the activated position.

Figure 9G:
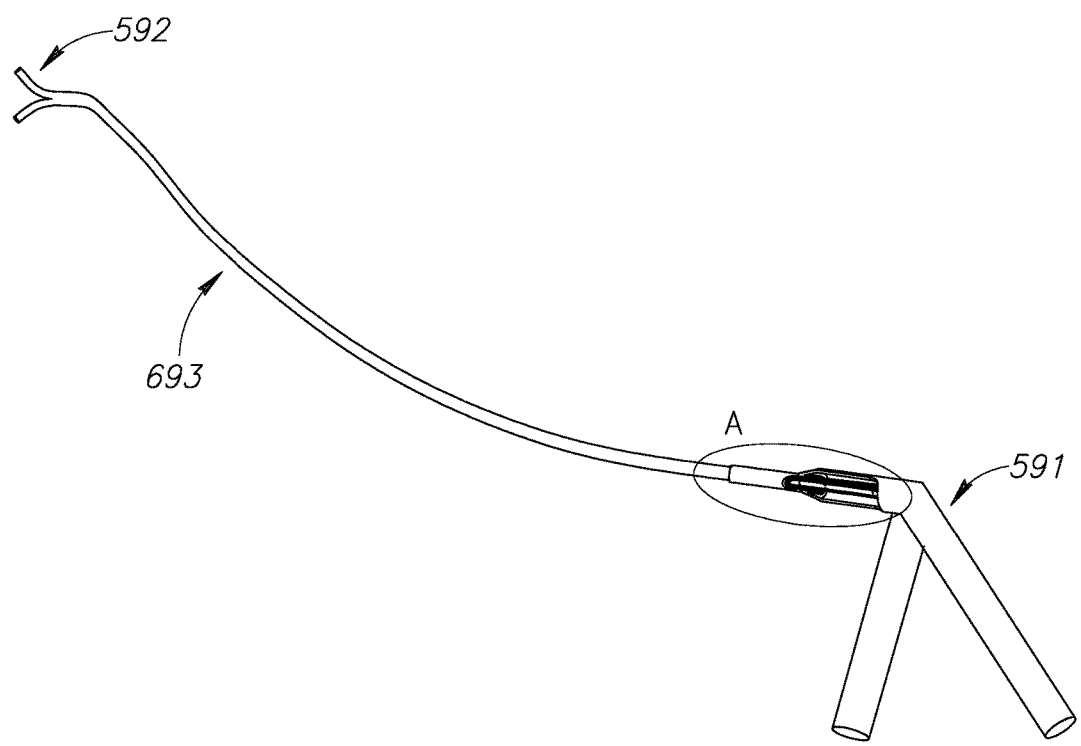

In reference to FIG. 9G, the tool 590 is shown alone. The distal end of the handle (591) and a portion of the tool body (693) immediately distal to the handle are shown in cutaway view.

Figure 9H:
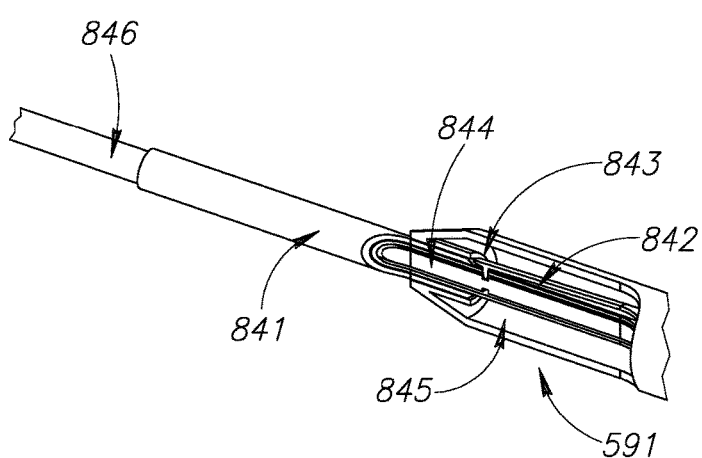

In reference to FIG. 9H, a close-up of area A (rectangle, FIG. 9G) is shown, illustrating a close-up of the distal end of the handle (591) and the proximal end of the tool body (693) with the microsurgical tool (590) in an activated state. The hook (843) approximately at the distal end of the latching mechanism (842) is held clear of the tool wall (846) and the depression (845) in the tool control transmission mechanism by the sleeve (841), thereby permitting rotation of the functional distal end of the tool relative to the tool wall. The extended distal tip (844) of the latching mechanism is adapted to allow smooth ingress of the sleeve (846) into the space between the latching mechanism (842) and the tool wall (846), facilitating raising the hook (843) to the activated state.

The hook (843) approximately at the distal end of the latching mechanism (842) can be positioned at the proximal end of the tool, at the distal end of the tool, or any combination thereof.

It should be pointed out that the profiled section of the channel (140) can be at the proximal end of the port, at the distal end of the port, all along the channel, in a portion of the body of the port, in the articulated section of the port, just proximal to the articulated section, or any combination thereof.

The profiled section of the tool can be at the proximal end of the tool, at the distal end of the tool, all along the tool, in the body of the tool, or any combination thereof.

It should be pointed out that according to the passive embodiment, the identification interface of the port is the profiled channels, such that only tool having a match fit (or at least partial fit) with said profiled channels of said port, will be defined as "allowed" tool and would be able to be introduced through said port and actuated in the same.

The following provides non limiting examples of active interfaces:
(a) a hook-and-latch mechanism, where the introduction of the tool into the mechanism lifts the latch and the tool is activated when the latch engages with the hook;
(b) a conductive region either on the tool of on the port, such that the introduction of the tool into the port completes an electrical circuit;
(c) a detector positioned either in the tool or the port, such that the introduction of the tool into the port reflects an electromagnetic radiation into said detector;
(d) an RFID tag positioned on the outer surface of the tool; and a tag reader positioned in the port; such that when the tool is introduced into the port the RF reader identifies the RFID tag. It should be pointed out that the RFID tag can be positioned on the port and the tag reader can be positioned on the tool.
(e) a bar code positioned on the outer surface of the tool; and a bar code reader positioned in the port; such that when the tool is introduced into the port the RF reader identifies the RFID tag. It should be pointed out that the bar code can be positioned on the port and the bar code reader can be positioned on the tool.
(f) a chip positioned on the outer surface of the tool; and a chip reader positioned in the port; such that when the tool is introduced into the port the RF reader identifies the RFID tag. It should be pointed out that the chip can be positioned on the port and the chip reader can be positioned on the tool.
(g) an optical/light emitting means positioned on the outer surface of the tool (the optical emitting means is adapted to emit light); and a detector for detecting a beam of light positioned in the port; such that when the tool is introduced into the port, the detector identifies a beam of light emitted from said optical emitting means. It should be pointed out that the optical emitting means can be positioned on the port and the detector can be positioned on the tool.

In operator-activated embodiments, an additional step is needed after insertion of the tool through the port in order to activate the tool. This additional step can comprise the operator lifting or closing a latch, pressing a button, moving a lever, moving a switch, uttering a predetermined voice command, entering a predetermined command via touch screen, entering a predetermined command via keyboard illuminating a portion of the tool, and any combination thereof.

In reference to FIG. 10, an articulating section (980) is shown at the distal tip of a port (10).

Figure 10A:
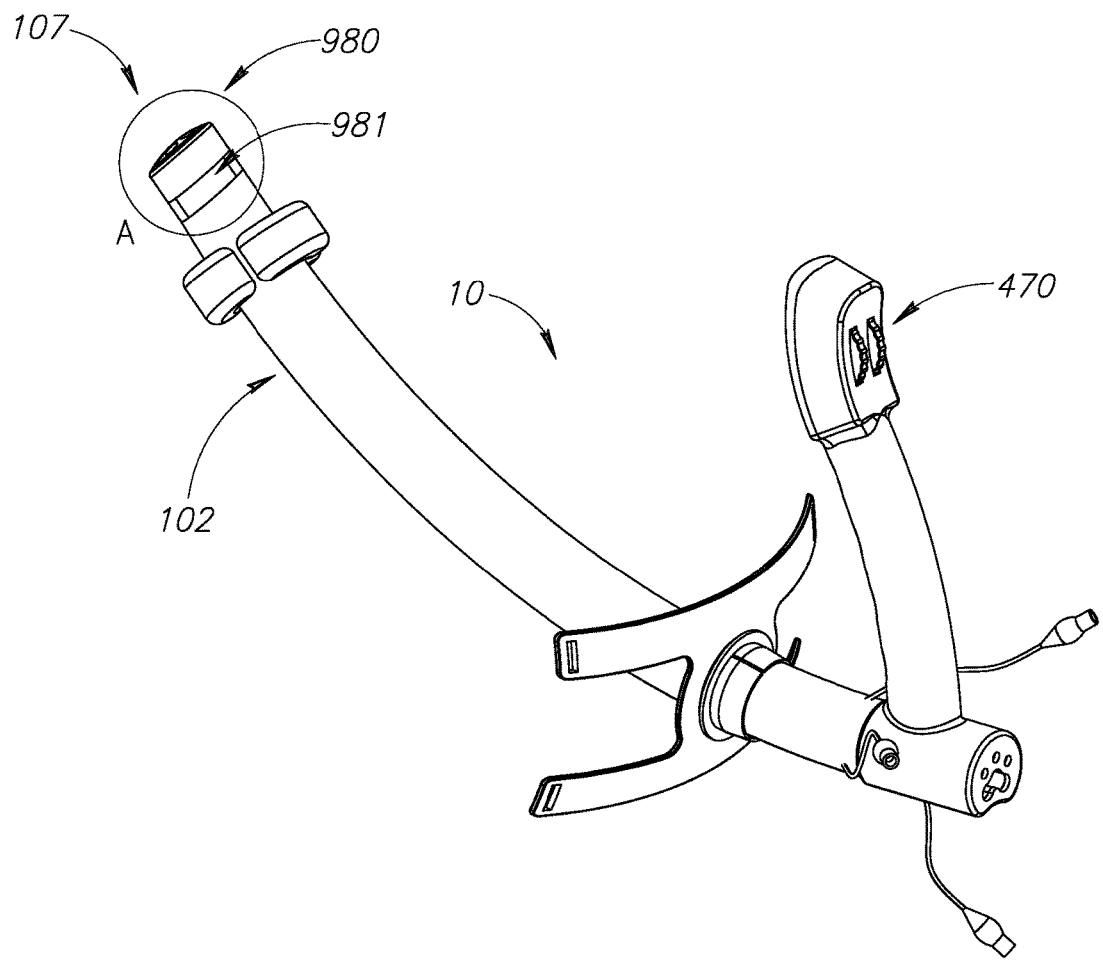
FIG. 10 illustrates an embodiment (not to scale) of an articulating distal tip.

In reference to FIG. 10A, the articulating section (980) comprises a portion of the port (10) approximately distal to the body, but proximal to the distal face (107). The articulating section (980) is of the same material as the remainder of the body of the port, but has a smaller diameter (981), thereby facilitating bending of the articulating section.

The distal face of the port (107) is in communication with the aiming control (470) on the handle of the port (10) so that the angle of the distal face with respect to the main longitudinal axis of the port (10) can be altered by the surgeon at will.

In further reference to FIG. 10A, the angle of articulation of the articulating section is 0; the main longitudinal axis of the articulating section is parallel to the main longitudinal axis of the port body and the distal face of the port is perpendicular to the main longitudinal axis of the port body.

In other embodiments, the distal face of the port is at an angle different from perpendicular to the main longitudinal axis of the articulating section. Change of the orientation of the distal face, however, is the same for all embodiments, as long as the angle of the distal face is fixed relative to the main longitudinal axis of the articulating section.

Figure 10B:
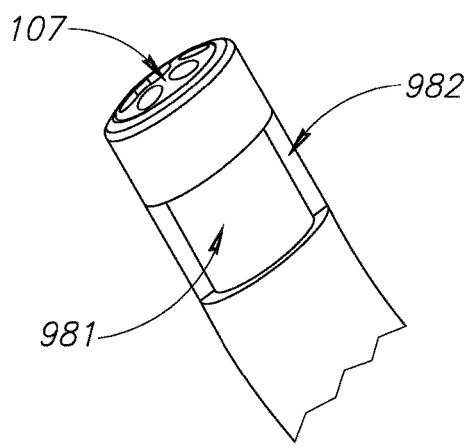

In reference to FIG. 10B, a close up of area A (circle, FIG. 10A), the distal portion of the port is shown, comprising the articulating section 980. The smaller diameter section (981) is surrounded by a cover (982) of a very soft material which does not interfere with the bending of the articulating section (981). The outer diameter of the cover is substantially the same as the outer diameter of the body of the port, thereby providing a smooth surface for the entire endoscope body and preventing sharp corners that have the potential to damage the patient, as well as crevices that can harbor bacteria.

In reference to FIG. 10C, the articulating section (980) has been bent counter-clockwise by 30 degrees and the distal face (107) is at an angle of 60 degrees to the main longitudinal axis of the port. The cover (982) for the narrow diameter section (981) is shown.

In reference to FIG. 10D, a close up of area A (circle, FIG. 10C), the distal portion of the port, is shown, comprising the articulating section 980. The articulating section (980) has been bent counter-clockwise by 30 degrees and the distal face (107) is at an angle of 60 degrees to the main longitudinal axis of the port. The cover (982) for the narrow diameter section (981) is shown.

The handle (460) comprises an aiming control (470) adapted to control the angle of the distal articulation section (480) relative to the body (102) of the device. The aiming control (470) can comprise a dial, a knob, a lever, a wheel, electronic mean, joystick, a sound detector adapted enable response to predetermined sounds, a light detector adapted to enable response to predetermined light patterns, any combination thereof, or any other means of controlling movement known in the art.

In a preferred embodiment, there is provided a communication mechanism for transmitting changes in the angle of the distal face from the control on the handle to the distal face of the port. This is at least one, and preferably four, strong cables running through the port from the control to the distal face. Moving the proximal end of the cables will move the distal end thereof, thereby rotating the distal face of the port. For non-limiting example, in an embodiment with four cables, one pair moves the distal face left-right, while the other pair moves it up-down.

Figure 11B:
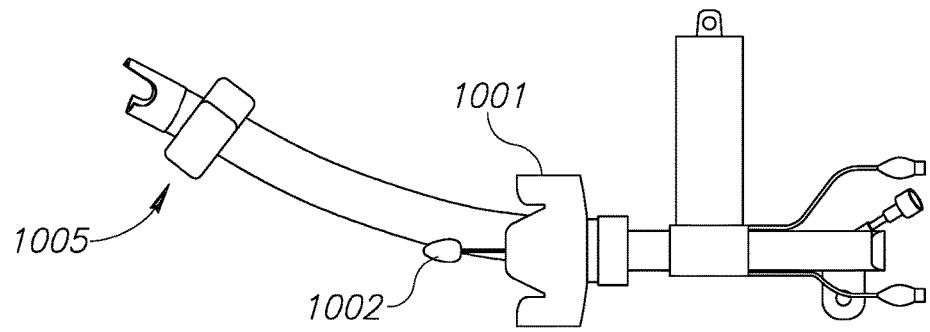
Figure 11C:
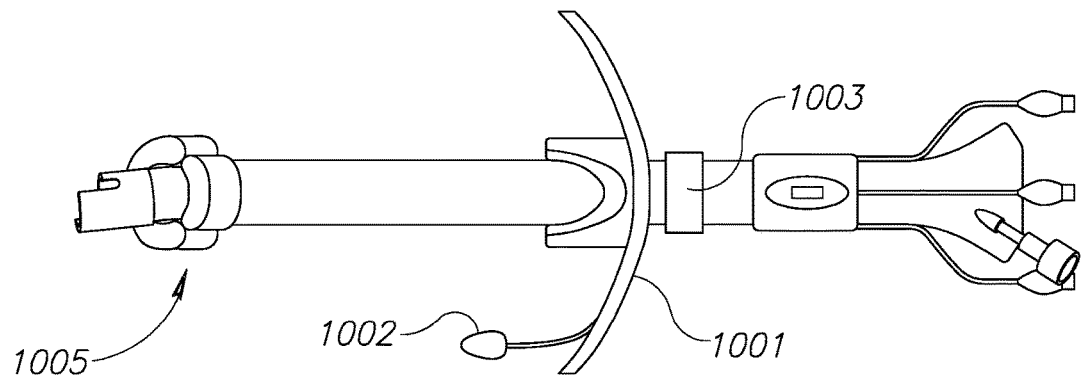
Figure 11D:
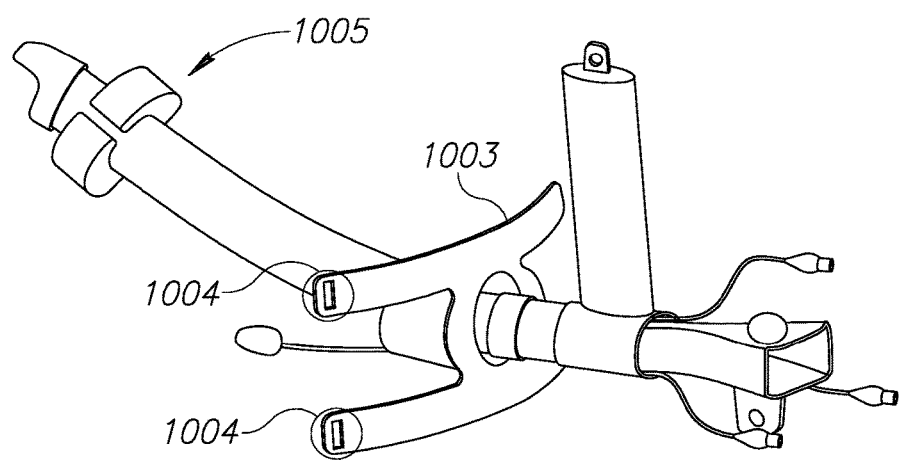

In other embodiments, inflatable cuffs, electric motors or piezoelectric actuators are used to effect changes in the angle of the distal face of the port. For the embodiments with electric motors or piezoelectric actuators, the communication mechanism is either wired or wireless. In some embodiments, the port further comprises at least one stabilization zone, for example, one near the proximal end (120, FIG. 1A; 1001, FIG. 11) of the port and one near the distal end (1005, FIG. 11) of the port.

In some embodiments the distal stabilization zone comprises a distal inflatable zone located near the distal end of the larygoscope or port. In some embodiments, the proximal stabilization zone comprises a second inflatable zone, a proximal inflatable zone. The balloon-like inflatable zones are made of a suitable biocompatible flexible material that expands on being filled with fluid. In a preferred embodiment, said fluid is air. In other embodiments, the fluid is an inert gas such as, but not limited to, nitrogen or argon. In yet other embodiments, it is oxygen. In yet other embodiments, a mixture of gases is used. In yet other embodiments, the gas mixture includes medically active materials, such as, but not limited to, anesthetics, analgesics or antibiotics. In further embodiments, the fluid is a liquid such as, but not limited to, water or saline solution. In some embodiments where the inflatable zone is filled with a liquid, the liquid includes medically active materials such as, but not limited to, anesthetics, analgesics or antibiotics. The fluid may also contain inert materials such as, but not limited to, stabilizers, anti-caking or anti-sticking agents, or preservatives.

In preferred embodiments of the invention, the inflatable zones are attached (e.g. by gluing) to a ring-like member, made of a relatively stiff biocompatible plastic, that is adapted to fit into the groove in which the inflatable zone sits. In most preferred embodiments, a pair of tabs are attached to the inner surface of the ring-like member, which are adapted to fit into slots, thus fixing the inflatable zone in place.

According to another embodiment of the present invention, the inflatable zones are an integral part of the larygoscope or port.

In the uninflated state, the outer diameter of the inflatable zones is no greater than the largest diameter of the body, so that the port can be inserted into the patient via the patient's oral cavity. In the inflated state, the outer diameter of the inflatable zones is sufficient to contact the inner surface of the patient's throat and/or hypopharynx. Each inflatable zone is in fluid connection with an inflation inlet located at the proximal end of the port. The inflation inlet is designed to allow introduction of air or other gas to inflate the inflatable zones and removal of air to deflate them. The inflation inlet is designed either to make a sealable connection with the gas source or to comprise a separate sealing means (e.g. by a valve). Any means for inflating the inflatable zones known in the art may be used instead.

The exact positioning of the inflatable zones along the length of the body is not vital to the operation of the port.

According to another embodiment of the present invention, either one of the distal/proximal inflatable zones has the ability to slide along the longitudinal axis of the port. Such an embodiment will allow exact positioning of the inflatable zones (namely, the balloons) by the surgeon.

In preferred embodiments, the proximal stabilization zone comprises a fixation and stabilization element adapted to fit over the patient's mouth, within the patient's mouth, over the lower part of the patient's face or any combination thereof.

According to another embodiment, the proximal stabilization zone is the fixation and stabilization element adapted to fit over the patient's mouth, within the patient's mouth, over the lower part of the patient's face or any combination thereof.

The main functions of the fixation and stabilization mechanism are the following:

(a) to stabilize and fixate the port in relation to the patient so that the port, once in place, will not move during microsurgery. It fixates its position and orientation. Such fixation is highly important as, during the procedure, tools are introduced through the port, which eventually results in friction between the tool and the port that can lead to an unwanted movement of the port.

(b) to stabilize and fixate the port to the patient's bed so as to prevent unwanted movements of either the head or the port.

According to another embodiment of the present invention, the fixation and stabilization element is a designed as a bite guard, adapted to both stabilize and fixate the port, but also to protect the teeth, tissues in the oral cavity, the tongue, the gingiva and any combination thereof.

Thus, the fixation and stabilization element stabilizes the port in relation to the patient and the patient's bed so that the port, once in place, will not move (left or right, up or down) during microsurgery.

In preferred embodiments, the fixation and stabilization element is made from flexible material and is of a shape and size that will fit to the human mouth and teeth.

According to one embodiment, it comprises a collar, adapted to fit around the port body and between the patient's upper and lower teeth. The collar is adapted to prevent the patient from biting the port, which could damage the patient's teeth or the port.

According to one embodiment, the fixation and stabilization element comprises a tongue catcher, adapted to catch and hold the tongue during the microsurgery.

Reference is now made to FIGS. 11A-D providing four different views of the fixation and stabilization element 1001 and the tongue catcher 1002. It should be emphasized that the main core concept behind the fixation and stabilization element 1001 is to fixate the port in place so as to prevent any unwanted movement of said port relative to the patient and the patient's bed.

FIGS. 11A-D further illustrate an embodiment of a distal stabilization zone (1005). In this embodiment, the distal stabilization zone comprises 3 inflatable elements, shown in the inflated state. The distal stabilization zone provides support, stability and anchorage to the port at its distal end.

In preferred embodiments, the distal stabilization zone (1005) is adapted such that the surgeon is able to "fine tune" the position of the port in the body orifice (e.g. the throat). For example, in the embodiment of FIGS. 11A-D, the surgeon can fine tune the position by selectively increasing or decreasing the amount of inflation of at least one of the inflatable zones. By, for non-limiting example, by increasing inflation of the inflatable zone (1005) uppermost in FIGS. 11A-D, the distal end of the port (10) is moved downward.

According to one embodiment, the fixation and stabilization element 1001 is able to slide along the port so that the distance between the distal and proximal stabilizations mechanisms is such that the body and distal end of the port rests stably and comfortably within the patient' mouth and throat, with the patient's head in a natural position.

In preferred embodiments, the fixation and stabilization element 1001 has at least one engagement mechanism 1003 characterized by two states, a locked state where the fixation and stabilization element 1001 is held in a fixed position relative to the port and a released state where the fixation and stabilization element 1001 is free to slide along the body of the port.

The engagement mechanism 1003 can comprise, but is not limited to, a radial clamping mechanism, a side screw pres sable into the body of the port, a spring which, when released, presses into the body of the port, a tightenable O-ring or any combination thereof.

In FIGS. 11A-D, a radial clamping or side screw embodiment of the engagement mechanism (1003) is shown.

According to another embodiment of the present invention, the fixation and stabilization element 1001 additionally comprises at least one groove 1004 (FIG. 11D) through which straps can be threaded. Said straps can be later attached to either the patient's head or bed, so as to fixate the position and orientation of the port to the patient's bed.

In preferred embodiments, the port further comprises an external fixation mechanism. This external fixation mechanism can comprise an airway control pillow, connection means to connect the airway control pillow to the port and, in preferred embodiments, a support bar or or frame.

The airway control pillow rests at least partly under the patient's head, supporting the patient's head such that the patient's airway is in the "sniffing position". The pillow places the head in this position by supporting the head and neck in a raised position such that the head is 7-8 cm above the bed the patient is lying on and the neck is about 11 cm from the same.

The fixation mechanism further comprises connection means adapted to connect the pillow to the port and possibly to a frame or bars attached to or resting on the bed, thereby ensuring that the larngoscope can not move relative to the patient's head.

The airway control pillow is connected to the patient and, in some embodiments, to the bar or frame, by any connection means well known in the art. Non-limiting examples of such connections means are flexible straps held in place by tying; by flexible straps held in place by loops at at least one end, said loops encircling at least one of a portion of the patient's head, the larygoscope, or the frame or bar; by Velcro straps; and by adhesive tape.

The handle is at least partly removable from the port. The removable portion of the handle is connected to the port by screws, pins, levers, latches, bayonet fittings, friction fittings or by any other means of releasably retaining demountable fittings known in the art.

In preferred embodiments, the port will comprise a built-in illumination device (not shown), which can be a light source (lamp or LED) attached to the distal end of the port or can be optical fibers traversing the port and carrying light from a source outside the port to the distal end of the same and thereby illuminating the field of view.

In preferred embodiments, the port has a plurality of channels, these channels can be:
1. A channel to accommodate a standard endoscopic camera (which has its own light source). The endoscopic camera is preferably a digital, distal chip endoscope that delivers high definition video images. The diameter of endoscopes is typically 3-4 mm so that the diameter of the channel should be at least 7 mm to prevent friction with the endoscope. Optionally, this channel will be designed such that it can accommodate endoscopes of different diameters. Preferably, this channel will not comprise any engagement interface so that any standard endoscopic camera can be used.
2. A preferably small diameter channel to provide ongoing suction, used to evacuate smoke or gas while using a laser or performing diathermy. The proximal outlet of this channel is preferably designed to attach to a standard suction tube.
3. Preferably at least two channels to accommodate the flexible, rotatable and articulating surgical tools. Since the surgeon has only two hands, two working channels normally suffice. The tools will comprise at least: triangular forceps, alligator forceps, scissors, a flexible, articulating laser hand-piece and a flexible, articulating suction handpiece in addition to or in place of the suction side-channel. The surgical tool can be selected from a group consisting of scissors, forceps, injection needle, dissector, laser, suction, and fiber optics or any other required surgical instrument.
4. A large diameter channel for removal of tissue specimens such as, but not limited to, vocal cord polyps or tumors. This channel could also be used for passage of absorbent pads for hemostasis. In some embodiments, this channel has a substantially larger diameter than the other channels. In other embodiments, the channel is enlargeable by removing part of its internal circumference.
5. Optionally, ay least one channel comprising optical fibers or an LED to provide additional light to the surgical field to prevent blocking or shadowing caused by the surgical tools.

In some embodiments, the port additionally comprises a plurality of inflatable gliding balloons mounted on a grooved rail attached to the outer circumference of the port and adapted to allow additional adaptation of the port to the patient's anatomy and to secure anchorage in the pharynx. The balloons will be positioned by the surgeon according the patient's anatomy to provide a broad surgical field, stable anchoring and positioning of the distal end of the port by selectively inflating the balloons.

In some embodiments, the device is provided in a plurality of standard sizes, including, but not limited to, a men's diameter, a women's diameter, a children's diameter and different lengths.

In some embodiments, the tools are 35-40 cm long, with an articulating section 1.5 to 3 cm long. The tools are no more than 3 mm in diameter. In some embodiments, the maximum articulation is 30 degrees. In other embodiments, it is 90 degrees. The tools can rotate around their main longitudinal axis through a full 360 degrees.

According to one embodiment, at least one channel within the port is adapted to deliver at least one medicament.

In light of the above, the advantages of the port of the present invention include:
1. The surgeon is able to position the camera and light source at any designated distance and any desired angle from the surgical field.
2. The endotracheal tube can be placed precisely at a desired position in relation to the port.
3. There is an invagination on one or more sides of the port to allow passage of endotracheal tubes.
4. Optionally, at least one channel comprising an engagement mechanism with gradable friction levels to allow comfortable sliding of the tools (and possibly endoscope) through the channels and also give better control and stability of movement.
5. The port is adapted to be firmly and safely fixed to the patient's head to fix its position and stabilize it.
6. Optionally, a locking mechanism providing safety with regards to the tool. In such embodiments, when the tools are locked (in-actuated), their functional distal ends can not move relative to the tool, thereby preventing damage to the tissues from unintentional movement of the functional distal end.
7. Safety with regards to the tools. Limitation of tool movements—reduces unwanted movement of the functional distal end due to tremor or vibration of the physician's hands.
8. Safety with regards to the tools. Limitation of movement of the port—unwanted movement of the port due to tremor or vibration of the physician's hands is prevented.

The port as described hereinabove has been adapted for use as a laryngoscope. In other embodiments, it can be adapted for use as a trochar or port system in other areas. Examples include, but are not limited to, laparoscopic surgery, intestinal surgery or examination where the point of entry is the anus, uterine surgery or examination where the point of entry is the vagina, bladder surgery or examination via the urethra and prostate surgery or examination via the urethra, and NOTES (Natural Orifice Transluminal Surgery).

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:
1. A laryngoscope for use in a patient, comprising:
a rigid S-shaped body having a distal end and a proximal end, wherein the body comprises
(i) at least one channel that extends throughout said S-shaped body and terminates at said proximal end of said body via an opening, the S-shaped body being configured to receive at least one flexible surgical tool through said opening of said channel at said proximal end, and
(ii) a plurality of internal channels that extend throughout said S-shaped body, the plurality of internal channels being configured to receive at least an endoscope and a light source within one or more of the plurality of internal channels towards the larynx of the patient; and
an extension disposed at the distal end of said S-shaped body, wherein said extension is configured to lift the epiglottis of the patient, thereby removing the epiglottis from a field of view of the endoscope.

2. The laryngoscope according to claim 1, wherein
the plurality of internal channels are at least three internal channels;
a first channel of the three internal channels is configured to accommodate the endoscope and the light source; and
said S-shaped body comprises, at its proximal end, two connectors each of the two connectors in communication with the remaining two of said three channels and configured to connect said remaining two channels to two handles of two flexible surgical tools, respectively, when the two flexible surgical tools are each inserted through one of said remaining two channels.

3. The laryngoscope according to claim 1, further comprising a mechanism for moving said extension in relation to the distal end of the body.

4. The laryngoscope according to claim 1, wherein said flexible surgical tool is selected from the group consisting of: scissors; forceps; an injection needle; a dissector; a flexible, articulating laser handpiece; and a flexible, articulating suction handpiece.

5. The laryngoscope according to claim 1, further comprising at least one balloon disposed distally over the body, wherein said balloon is in fluid communication with an inlet disposed at the proximal end of the body and is configured to contact the walls of the hypopharynx upon inflation.

6. The laryngoscope according to claim 1, wherein said body comprises an external longitudinal groove configured to accommodate an intubation tube.

7. The laryngoscope according to claim 1, further comprising afixation and stabilization element disposed at a proximal end of said body and configured to affix said body in relation to the patient, wherein said fixation and stabilization element is configured to fit over the patient's mouth, within the patient's mouth or over the lower part of the patient's face.

8. The laryngoscope according to claim 1, further comprising a tongue catcher.

9. The laryngoscope according to claim 1, further comprising a tool identification portion configured to allow only identified tools to pass through at least one of the plurality of channels.

10. The laryngoscope according to claim 9, wherein said identification mechanism is selected from the group consisting of a barcode reader, an RFID (Radio Frequency Identification) tag reader and a light detector.

11. A method for surgery, comprising:
a) obtaining a laryngoscope which comprises:
a rigid S-shaped body having a distal end and a proximal end, wherein the body comprises (i) at least one channel that extends throughout said S-shaped body and terminates at said proximal end of said body at an opening, the S-shaped body being configured to receive at least one flexible surgical tool through said opening of said channel at said proximal end; and (ii) a plurality of internal channels that extend throughout said S-shaped body, and
an extension disposed at the distal end of said body;
b) introducing a portion of said laryngoscope into the oral cavity of a patient, such that said extension lifts the epiglottis of the patient and the distal end of said body reaches the hypopharynx of the patient; and
c) inserting at least an endoscope, a light source and a flexible surgical tool through said at least one internal channel and towards the larynx of the patient.

12. The method according to claim 11, wherein:
the plurality of internal channels are three internal channels;
a first channel of the three internal channels is configured to accommodate the endoscope and the light source; and
said S-shaped body comprises, at its proximal end, two connectors each of the two connectors in communication with the remaining two of said three channels and configured to connect said remaining two channels to two handles of two flexible surgical tools, respectively, when the two flexible surgical tools are each inserted through one of said remaining two channels.

13. The method according to claim 11, wherein said laryngoscope further comprises a mechanism for moving said extension in relation to the distal end of the body, and wherein the method further comprises moving said extension in relation to the distal end of the body.

14. The method according to claim 11, wherein said flexible surgical tool is selected from the group consisting of: scissors; forceps; an injection needle; a dissector; a flexible, articulating laser handpiece; and a flexible, articulating suction handpiece.

15. The method according to claim 11, wherein said laryngoscope further comprises at least one balloons disposed distally over the body, wherein said balloon is in fluid communication with an inlet disposed at the proximal end of the body, and wherein the method further comprises inflating said balloon such that it contacts the walls of the hypopharynx.

16. The method according to claim 11, wherein said body comprises an external longitudinal groove configured to accommodate an intubation tube, and wherein the method further comprises inserting an intubation tube into the trachea of the patient through said groove.

17. The method according to claim 11, wherein said laryngoscope further comprises a fixation and stabilization element disposed at a proximal end of said body, and wherein the method further comprises affixing said body in relation to the patient by fitting said fixation and stabilization element over the patient's mouth, within the patient's mouth or over the lower part of the patient's face.

18. The method according to claim 11, wherein said laryngoscope further comprises a tongue catcher, and wherein the method further comprises catching and holding the tongue of the patient using said tongue catcher.

19. The method according to claim 11, wherein said laryngoscope further comprises a tool identification portion, and wherein the method further comprises using said identification portion to allow only identified tools to pass through at least one of the plurality of channels.

20. The method according to claim 19, wherein said identification mechanism is selected from the group consisting of a barcode reader, an RFID (Radio Frequency Identification) tag reader and a light detector.

* * * * *